United States Patent [19]

Kupper et al.

[11] Patent Number: 4,851,588
[45] Date of Patent: Jul. 25, 1989

[54] NOVEL PROCESS FOR THE PREPARATION OF BRONOPOL

[75] Inventors: Robert J. Kupper, Mt. Airy; Felek Jachimowicz, Columbia; Jennifer M. Quirk, Highland, all of Md.; Christer L. Hakansson, Helsingborg, Sweden

[73] Assignee: W. R. Grace & Co.-Conn., New York, N.Y.

[21] Appl. No.: 210,675

[22] Filed: Jun. 23, 1988

[51] Int. Cl.$^4$ .............................................. C07C 79/18
[52] U.S. Cl. .................................... 568/713; 568/704
[58] Field of Search ................................ 568/704, 713

[56] References Cited

U.S. PATENT DOCUMENTS 3,658,921 4/1972 Wessendorf et al. ............... 568/704
3,711,561 1/1973 Wessendorf ......................... 568/704

Primary Examiner—Werren B. Lone
Attorney, Agent, or Firm—Howard J. Troffkin

[57] ABSTRACT

A process of forming 2-bromo-2-nitro-1,3-propanediol by contacting a 5-nitro-1,3-dioxane with bromine under alkaline conditions and hydrolyzing the brominated product.

20 Claims, No Drawings

NOVEL PROCESS FOR THE PREPARATION OF BRONOPOL

BACKGROUND OF THE INVENTION

The present invention relates to a novel process to form 2-bromo-2-nitro-1,3-propanediol (commonly known as "bronopol"). The present process provides a means of forming bronopol using readily obtained materials under mild and easily handled conditions suitable for industrial application.

Bronopol is a highly desired material utilized as a biocide and as a medicament in toiletries such as shampoos and the like.

Bronopol has been previously prepared from 2-oximino-1,3-propanediol, 2-nitro-1,3-propanediol, and oximinomalonic acid diethyl ester. In most cases the required processes provided low yields and, in certain instances, utilizes poorly accessible starting materials. In addition, the processes normally entail the generation of decomposable and dangerous intermediates which require special equipment and handling practices. The expense of the reactants and equipment required, as well as the special handling needed leads to unsatisfactory processes for industrial application.

The major commercial method of producing bronopol is disclosed in U.S. Pat. Nos. 3,658,921 and 3,711,561. The process entails the initial formation of sodium 2-nitro-1,3-propanediol by reacting formaldehyde with nitroemethane and with an alkali metal hydroxide such as sodium hydroxide. The formed idol must then be added slowly to an appropriate amount of bromine to produce the desired bronopol. The difficulty with this method relates to the sodium nitro-1,3-propanediol which is known to be an unstable material which decomposes with catastrophic results.

It is highly desired to have a process capable of forming bronopol which utilizes readily available and easily handled materials.

SUMMARY OF THE INVENTION

The present invention is directed to a process which is readily adaptable to industrial application and utilizes reactants and conditions which do not present a handling problem.

The instant process comprises bromination of certain 5-nitro-1,3-dioxanes under certain conditions described below to form the corresponding 5-bromo-5-nitro derivative and hydrolyzing the brominated derivative to give the desired bronopol.

DETAILED DESCRIPTION OF THE INVENTION

The present process provides the desired bronopol using readily available reactants under conditions easily adoptable for industrial application.

The total synthesis can be accomplished by the following reactions:

1. Nitromethane is reacted with three moles of formaldehyde to form tris(hydroxymethyl)nitromethane (I).

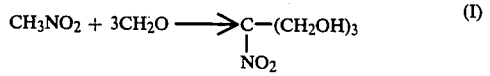

This Henry Reaction is carried out by contacting the nitromethane and formaldehyde in a solvent normally selected from a lower alkyl alcohol or water (preferably methanol) in the presence of a catalytic amount of base such as sodium or potassium hydroxide. The formaldehyde should be present in at least stiochiometric amounts based on nitromethane (i.e. 3 moles of formaldehyde per mole of nitromethane). This reaction is known and the product can be commercially obtained. This product, unlike the dihydroxymethyl nitromethane sodium salt used in U.S. Pat Nos. '921 and U.S. Pat. No. '561, is a stable product which is readily obtained in very high yields because the substitution is allowed to go to completion.

2. The formed tris(hydroxymethyl)nitromethane (I) is then reacted with a ketone in the presence of a catalytic amount of a strong acid to form the corresponding acetal, the 5-hydroxymethyl-5-nitro-1,3-dioxane which has substitution in the 2 position (II), in good yields.

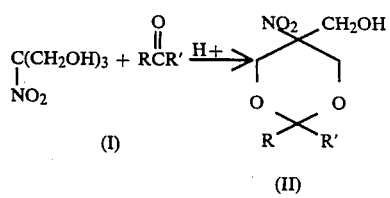

Each R and R' can independently be selected from hydrogen or an alkyl, cycloalkyl or aryl group or R and R' can together form an alkylene group, and preferably a $C_4$-$C_6$ alkylene group. The particular identity of R and R' is not critical to this reaction nor to the overall synthesis. However, the dialkyl ketones are preferred due to their availability. Examples of suitable ketones include acetone, methyl ethyl ketone, diethyl ketone, cyclohexanone and the like. The reaction can be run neat using excess ketone as the reaction medium (preferred) or by using an inert solvent in which both compound I and the ketone are soluble. The reaction is catalyzed by the presence of catalytic amounts (normally from about 0.001 to 1 weight percent based on the weight of ketone) of a strong acid, such as a mineral acid (HCl $H_2SO_4$, and the like) or a strong organic acid such as glacial acetic acid, toluene sulfonic acid and the like.

The above reaction (2) produces water as a by-product. The water must be removed in order to prevent reversion of the formed acetal back to the ketone and alcohol. When the reaction utilizes a high boiling ketone (having a B.P. higher than water and suitable for separating the water from ketone by distillation), such as cyclohexanone, the water by-product can be removed by azeotropic distillation during the progress of the reaction. When a low boiling ketone, having a boiling point lower than water, such as acetone, is used the procedure requires the presence of a dessicant, such as boron trifluoride etherate or a molecular sieve which collects water or the like to remove the water as it forms.

Although the above reaction utilizes readily attainable and inexpensive reactants, the need to remove the water by-product as it forms may add to the cost of the reaction and the overall synthesis. If such economics presents a factor, the formation of an acetal can be accomplished without the production of water by alternate reactions, as described hereinbelow.

2(A). The tris(hydroxymethyl)nitromethane (I) can be converted to an acetal by reacting it with a vinyl ether in the presence of a catalytic amount of a strong acid (such as mineral acids, glacial acetic acid and the like) by the following reaction:

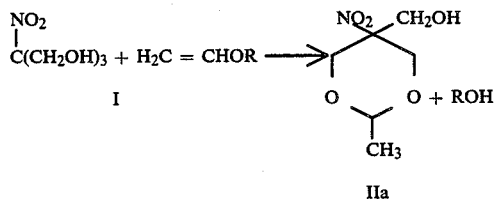

R can represent any alkyl, cycloalkyl or aryl group and is preferably a lower alkyl. Examples of suitable vinyl ethers include ethyl vinylether, methyl vinylether and the like. The resultant by-product alcohol does not interfere with the reaction.

2(B). Again, as an alternate means, the desired acetal compound can be provided by reacting the tris(hydroxymethyl)nitromethane (I) with certain gem diethers in the presence of a catalytic amount of a strong acid (such as mineral acid, glacial acetic acid and the like) by the following reaction:

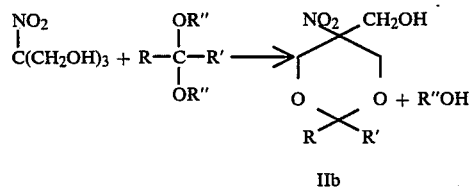

The symbols, R and R' are the same hydrocarbon as described above with respect to reaction 2 and R'' can be any alkyl, preferably a lower alkyl such a methyl, ethyl, propyl and the like. Examples of such gem ethers include 2,2-dimethoxypropane 2,2-diethoxypropane, 3,3-dimethoxypentane, 3,3-diethoxy pentane and the like.

The reaction 2A and 2B can be carried out by taking up compound I in excess of the ether and warming the system to a temperature of from about 20° C. to 80° C. with temperatures of from 20° C. to 50° C. being preferred.

The resultant acetals, (II), (IIa) and (IIb), are all readily formed in good yields which is normally greater than about 90 percent. The acetal can be separated from the reaction mixture by conventional means such as by distillation where the product is a liquid or by filtration where the product is a solid. The exact nature of the product depends on the identity of R and R'.

3. The 5-hydroxymethyl-5-nitro-1,3-dioxane derivatives (II), (IIa) or (IIb) are readily converted into the corresponding 5-nitro-1,3-dioxane compound by treating the derivative with alkali, such as an alkali (preferably) or alkaline earth metalhydroxide (MOH), and then acidification of the solution according to a procedure suggested in Roczniki Chemii Ann. Soc. Chim. Polonorum 47 409 (1973) as represented by the conversion of (II) as follows:

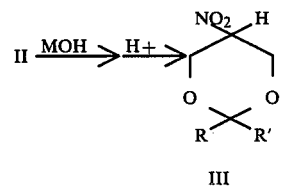

The reaction can be carried out by taking the acetal up in an aqueous solution of an alkali metal hydroxide such as sodium or potassium hydroxide. The hydroxide concentration may be from about 5 to 25 percent or greater with from 10 to 20% being preferred. The presence of excessive amounts of water (above that required to retain a solution) should be avoided. The solution should be agitated as by stirring for a period of time of from 10 minutes to 200 minutes, with from about 30 to 100 minutes normally being satisfactory, while maintaining an elevated temperature of from about 30° to 100° C. (40°-80° C. being preferred). The solution is then cooled to a reduced temperature to less than about 20° C. and preferably from about 0° C. to 20° C. prior to slow introduction of the acid. Although concentrated mineral acid can used, it is preferred to use a strong organic acid to minimize the water concentration and thereby enhance the precipitation of product III which can be readily separated by conventional means such as filtration. When product IIa is used the resultant product will be the corresponding 2-substituted-5-nitro-1,3-dioxane(IIIa).

The 5-nitro-1,3-dioxane derivative III or IIIa, whether formed by the above synthesis route or by other methods (such as one proposed by Linden et al., J. Org. Chem. 21 1175 (1956) by direct cyclization of 2-nitropropanediol-1,3) has been found to be readily convertible into bronopol. The process requires the bromination of a product III or IIIa followed by hydrolysis of the resultant brominated material.

4. The product III or IIIa is taken up in a liquid which is inert to akali and/or bromine and which is a solvent for the nitronate salt initially formed. Such liquids include water, tertiary alcohols, such as t-butylalcohol and the like; sulfoxides, such as dimethylsulfoxide and the like; and amides such as dimethylfomamide, dimethylacetamide and the like. The most preferred material is water.

Compound III or IIIa is introduced into an aqueous solution containing at least a stoichiometric equivalent of an alkali metal hydroxide (MOH) such as sodium hydroxide, potassium hydroxide and the like. Normally, excess amounts (preferably, up to about 1.1 mole per mole of compound III or IIIA) of the hydroxide is used. The concentration of hydroxide in the aqueous solution is normally from about 5 to 30 percent. Contacting of the alkali metal hydroxide and compound (III) or (IIIa) can be accomplished under temperatures from about 10° C. to about 100° C. with from about 20° to 60° C. being preferred. The reaction can be conducted at ambient conditions. The sodium nitronate salt is soluble in aqueous solution and provides a stable intermediate material which can be directly brominated. The bomination is accomplished by introducing liquid bromine into the aqueous solution in at least stoichiometric amounts based on the amount of compound (III) or (IIIa) being treated. Small excesses of bromine will be consumed by any excess of the alkali metal hydroxide present in the solution. The bromination is exothermic and should be maintained at temperatures of from 5° C. to 50° C. with from 10° C. to 30° C. being preferred. Control can be readily accomplished by any conventional means such as by incremental introduction of bromine, the use of a cooling means in or surrounding the reaction vessel or the like.

Alternately, the bromination can be conducted by the cointroduction of an alkali metal hydroxide (MOH) and bromine liquid into a suspension of compound (III) or (IIIa) (i.e. an aqueous suspension). The resultant 5-bromo-5-nitro-1,3-dioxane derivatives (IV) are insoluble in the required solvent and, therefore, are readily separated and recovered, if desired, by filtration. The overall reaction is represented as follows:

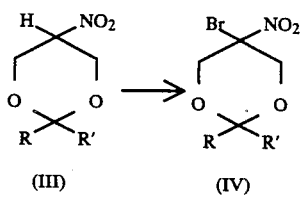

(III)  (IV)

Alternately to reactions 3 and 4 as described hereinabove, the acetal compund (II), (IIa) or (IIb) can be directly converted into the corresponding 5-bromo-5-nitro-1,3-dioxane derivative IV by taking up the acetal II, IIa or IIb in a liquid which is inert to base and bromine as described above. Water is the preferred liquid. The acetal is reacted with a molar excess of an alkali metal hydroxide. as described with respect to reaction 3 above. The resultant solution is cooled to a temperature of from about 10° C. to 50° C. (preferably from about 10° C. to 30° C.) and liquid bromine is added to the solution while maintaining the lowered temperature as described with respect to reaction 4 above. The resultant 5-bromo-5-nitro-1,3-dioxane derivative (IV) is separated from the reaction media by conventional methods such as by filtration, or evaporation of the liquid media or the like.

5. Bronopol is recovered in good yields by contacting product IV with a strong acid.

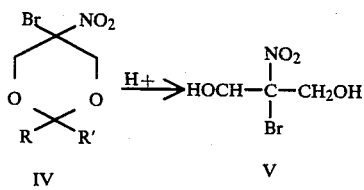

IV   V

The formation of bronopol from product IV proceeds readily by taking product IV up in water (preferred) or a lower alkyl alcohol such as methanol, ethanol, propanol or the like to provide a solution and introducing a mineral acid such as hydrochloric, sulfuric acid into the solution. Although the exact mode of contacting the acid and product IV is not critical, it is preferred that the acid be introduced slowly and the solution be maintained at moderate temperatures such as ambient to 75° C., preferably from 30 to 50° C. Small amounts of acid is sufficient and may normally be from 0.01 to 0.1 mole per mole of product IV. Larger amounts of acid may be used but is normally unnecessary. Bronopol can be recovered from the solution by any conventional manner such as by evaporation of the liquid solvent, or by use of a non-solvent to precipitate the product V, or other conventional means. Bronopol is known to be soluble in water, lower alcohols and ethylacetate and substantially insoluble in liquids such as chloroform, acetone, diethylether, benzene, ligroin and the like.

The subject process provides a new route for the production of bronopol using readily available and easily attainable reactants. The process requires conventional handling conditions which do not present any problems which may result in catastrophic results, such as encountered by the present commercial mode of forming bronopol.

The present process provides a means of converting 5-nitro-1,3-dioxane derivatives into bronopol by deprotonation and bromination under certain conditions which retain the dioxane ring and then hydrolyzing the resultant brominated derivative. Further, the present invention provides a process for synthesizing bronopol starting with nitromethane and without encountering the hazardous material, sodium bis(hydroxymethyl)nitromethane, of the present commercial process.

The following examples are given for illustrative purposes only and are not meant to be a limitation on the invention as defined by the claims appended hereto. All parts and percentages are by weight unless otherwise indicated.

EXAMPLE 1

A 100 ml round bottom flask equipped with a stir bar and reflux condenser topped with a nitrogen inlet was charged with 15.1 g (0.1 mol) of tris(hydroxymethyl) nitromethane and 22 ml (0.3 mol) of acetone. The mixture was heated until all the tris(hydroxymethyl)nitromethane had dissolved and then was cooled to 15°–20° C. The trimethylol compound crystallized in fine needles. Boron trifluorideetherate (13 ml, 0.1 mol) was added with stirring. The temperature rose to 55° C. and crystals of product began to separate. After five minutes, the mixture was poured into a stirred mixture of 110 ml of saturated sodium bicarbonate solution and excess ice. After stirring for 15 minutes, the product, 2,2-dimethyl-5-hydroxymethyl-5-nitro-1,3-dioxane was collected by filtration, washed with cold water and dried in vacuo. The yield was determined to 88%.

EXAMPLE 2

To a 100 ml round bottom flask equipped with a stir bar, soxhlet extractor and reflux condensor topped with a nitrogen inlet was added 2 g (0.013 mol) tris)hydroxymethyl)nitromethane, 1.42 g (0.014 mol) cyclohexanone, 0.2 g p-toluenesulfonic acid and 60 ml acetonitrile. The soxhlet thimble was filled with 3A molecular sieves. The reaction mixture was then refluxed for 24 hours with the sieves being changed at 6 hours. After cooling to room temperature, all volatiles were removed in vacuo. The solid remaining was then dissolved in 30 ml CH₂Cl₂ and dried over MgSO₄. After one hour, the MgSO₄ was filtered off and the CH₂Cl₂ removed to give 2,2-pentamethylene-5-hydroxymethyl-5-nitro-1,2-dioxane in 73% yield.

EXAMPLE 3

Into a 250 ml round bottom flask equipped with a stir bar, thermometer and reflux condensor topped with a nitrogen inlet was added 5.73 g (0.03 mole) of 2,2-dimethyl-5-hydroxymethyl-5-nitro-1,3-dioxane and 70 ml 10% sodium hydroxide which was heated to 60° C. for one hour. The solution was cooled to 5° C. and at this temperature acidified to pH 5 with concentrated acetic acid. The precipitated solid was filtered off and dried to give 5.2 g (92%) of 2,2-dimethyl-5-nitro-1,3-dioxane m.p. 60°-61° C. ¹H NMR in CD₃OD also confirmed the structure.

EXAMPLE 4

The reaction was run as described in Example 3 except that 2,2-pentamethylene-5-hydroxymethyl-5-nitro-1,3-dioxane was used instead of 2,2-dimethyl-5-hyroxymethyl-5 -nitro-1,3-dioxane. The yield of product 2,2-pentamethylene-5-nitro-1,3-dioxane was 81%.

EXAMPLE 5

Into a 25 ml round bottom flask was placed 5 ml of water amd 900 mg of (5.6 mmoles) of 2,2-dimethyl-5-nitro-1,3-dioxane as formed in Example 3 above. The resulting suspension was stirred and cooled to 10° C. Seven ml of 1 N sodium hydroxide solution was added incrimentally over a short time period. All of the compound went into solution. The solution was then treated with 895 mg of liquid bromine. A solid separated from the solution with disappearance of the bromine color. The resultant suspension was stirred for about 10 minutes after all of the bromine was added and then extracted with two portions of 5 ml of dicloromethane and then tried over MgSO₄ with 50 mg of charcoal (Norite A), filtered and dired in vacuum at 25° C. to give 1.28 gm (95.2%) of pure white crystals having a MP of 83°-85° C. and a 'H NMR consistant with 2,2-dimethyl-5-bromo-5-nitro-1,3-dioxane.

EXAMPLE 6

The reaction is run as described in Example 5 except that 2,2-pentamethylene-5-nitro-1,3-dioxane is used instead of 2,2-dimethyl-5-nitro-1,2-dioxane. The yield of product is similar to that obtained in Example 5.

EXAMPLE 7

To a 50 ml round bottom flask equipped with a stir bar and reflux condensor topped with a nitrogen inlet was added 0.5 g (.004 mol) 2,2-dimethyl-5-nitro-5-bromo-1,3-dioxane, 10 ml methanol and 0.3ml concentrated HCl. The reaction was heated to 35°-40° C. for 1 hour. After cooling to room temperature, the volatiles were removed to give crystalline bronopol (95% yield) which on recrystallization from acetone had a melting point of 120° C.

EXAMPLE 8

Into a 25 ml round bottom flask is placed 5 ml of water and 1070 mg (5.6 mmoles) of 2,2-dimethyl 5-hydroxymethyl-5-nitro-1,3-dioxane as formed in Example 2 above. The resulting suspension is treated with 13 ml of 10% sodium hydroxide solution and heated to 60° C. for one hour to form a solution. The solution is cooled to 10° C. and treated with 895 mg of liquid bromine. A solid separates from solution with disappearance of bromine color. The resultant suspension is extracted with several portions of dicloromethane and then dried with over MgSO₄, filtered and dried under vacuum at 25° C. to produce the 5-bromo-5-nitro derivative as in Example 5 above.

We claim:

1. A process for forming 2-bromo-2-nitro-1,3-propanediol which comprises brominating a 5-nitro-1,3-dioxane compound of the formula

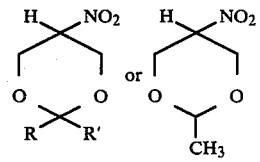

wherein each R and R' is independently selected from hydrogen, alkyl, cycloalkyl, aryl or where R and R' together represents an alkylene group, by contacting said 5-nitro-1,3-dioxane with bromine under alkaline conditions and at temperatures of from 5° C. to about 50° C. to form a corresponding 5-bromo-5-nitro-1,3-dioxane compound and hydrolyzing said 5-bromo-5-nitro-1,3-dioxane compound by contacting it with an acid selected from a mineral or strong organic acid.

2. The process of claim 1 wherein the bromination comprises contacting said 5-nitro-1,3-dioxane compound with liquid bromine in the presence of an alkali metal hydroxide and wherein the hydrolysis of the brominated product comprises contacting a solution of said product with small amounts of an acid selected from mineral acids and strong organic acids.

3. The process of claim 1 wherein the bromination is conducted by contacting an aqueous suspension of said 5-nitro-1,3-dioxane compound with an alkali metal hydroxide at a temperature of from about 10° to 100° C. and subsequently introducing liquid bromine into the system while maintaining a temperature of from about 10° C to about 50° C.

4. The process of claim 2 wherein the bromination is conducted by contacting an aqueous suspension of said 5-nitro-1,3-dioxane compound with an alkali metal hydroxide at a temperature of from about 10° to 100° C. and subsequently introducing liquid bromine into the system while maintaining a temperature of from about 10° C to about 50° C.

5. The process of claim 1 wherein the bromination comprises contacting said 5-nitro-1,3-dioxane compound with liquid bromine and alkali while maintaining the temperature at from about 10° C. to 50° C.; said bromine and alkali each being present in at least molar equivalence with respect to said dioxane compound.

6. The process of claim 2 wherein the bromination comprises contacting said 5-nitro-1,3-dioxane compound with liquid bromine and alkali while maintaining the temperature at from about 10° C. to 50° C.; said bromine and alkali each being present in at least molar equivalence with respect to said dioxane compound.

7. The process of claim 1 wherein the hydrolysis is conducted by contacting the 5-bromo-5-nitro-derivative of said dioxane compound with a mineral acid.

8. The process of claim 2 wherein the hydrolysis is conducted by contacting the 5-bromo-5-nitro-derivative of said dioxane compound with a mineral acid.

9. The process of claim 3 wherein the hydrolysis is conducted by contacting the 5-bromo-5-nitro-derivative of said dioxane compound with a mineral acid.

10. The process of claim 5 wherein the hydrolysis is conducted by contacting the 5-bromo-5-nitro-derivative of said dioxane compound with a mineral acid.

11. A process of forming 2-bromo-2-nitro-1,3-propanediol which comprises (a) reacting nitromethane with formaldehyde in the presence of a catalytic amount of a base to form tris(hydroxymethyl)nitromethane(I);

(b) reacting I with a ketone of the formula

in the presence of a catalytic amount of a strong acid and under conditions to remove water by-product as formed to produce a 5-nitro-5-hydroxymethyl-1,3-dioxane compound (II) of the formula

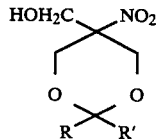

wherein each R and R' are independently selected from hydrogen, alkyl, cycloalkyl or aryl groups or R and R' together represent an alkylene group;
(c) reacting (II) with a molar excess of an alkali or alkaline metal hydroxide and with a molar excess of liquid bromine with respect to the molar concentration of II at temperatures of from about 10° C. to about 50° C. to produce 5-bromo-5-nitro-1,3-dioxane derivative (IV) of the corresponding II reactant; and
(d) hydrolyzing IV by contacting a solution of IV with an acid selected from mineral acids and a strong organic acid to produce 2-bromo-2-nitro-1,3-propanediol.

12. A process of forming 2-bromo2-nitro-1,3-propanediol which comprises
(a) reacting nitromethane with formaldehyde in the presence of a catalytic amount of a base to form tris(hydroxymethyl)nitromethane(I);
(b) reacting I, in the presence of a catalytic amount of a strong acid, with an ether compound selected from (a) a vinyl alkyl ether of the formula CH$_2$=CHOR (wherein R represents alkyl, cycloalkyl or aryl) or (b) a gem diether of the formula

(wherein R and R' are as defined below and R" represents an alkyl) to produce a 5-nitro-5-hydroxymethyl-1,3-dioxane (II) of the formula:

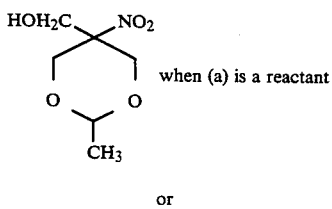

or

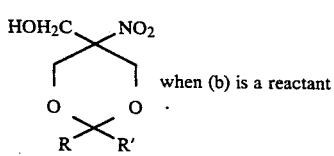

wherein each R and R' are independently selected from hydrogen, alkyl, cycloalkyl or aryl groups or R and R' together represent a C$_4$-C$_6$ alkylene group;
(c) reacting (II) with a molar excess of an alkali or alkaline earth metal hydroxide with a molar excess of liquid bromine with respect to the molar concentration of II at temperature of from about 10° C. to about 50° C. to produce 5-bromo-5-nitro-1,3-dioxane derivative (IV) of the corresponding II reactant; and
(d) hydrolyzing IV by contacting a solution of IV with an acid selected from mineral acid and a strong organic acid to produce 2-bromo-2-nitro-1,3-propanediol.

13. The process of claim 11 wherein said steps (c) and (d) comprise reacting (II) with an alkali metal hydroxide at elevated temperatures and neutralizing said alkali metal with an organic acid at reduced temperatures of less than about 20° C. to produce 5-nitro-1,3-dioxane derivative (III) of the corresponding (II) reactant; contacting (III) with bromine in the presence of alkali and at temperatures of from about 10° to 50° C. to produce the 5-bromo-5-nitro-1,3-dioxane derivative (IV) of the corresponding (III) reactant; and hydrolyzing (IV) by contacting a solution of (IV) with a mineral acid to produce 2-bromo-2-nitrol-1,3-propanediol.

14. The process of claim 12 wherein said steps (c) and (d) comprise reactig (II) with an alkali metal hydroxide at elevated temperatures and neutralizing said alkali metal with an organic acid at reduced temperatures of less than about 20° C. to produce 5-nitro-1,3-dioxane derivative (III) of the corresponding (II) reactant; contacting (III) with bromine in the presence of alkali and at a temperature of from about 10° to 50° C. to produce the 5-bromo-5-nitro-1,3-dioxane derivative (IV) of the corresponding (III) reactant; and hydrolyzing (IV) by contacting a solution of (IV) with a mineral acid to produce 2-bromo-2-nitro-1,3-propanediol.

15. The process of claim 11 wherein in (a) the formaldehyde is used in at least 3 moles for each mole of nitromethane; and in (b) the ketone is selected from a low boiling ketone with a dessicant to remove formed water or the ketone is selected from a high boiling ketone and formed water is removed by distillation.

16. The process of claim 12 wherein in (a) the formaldehyde is present in at least 3 moles for each mole of nitromethane; in b) the ether is selected from ethyl vinyl ether, 2,3-dimethoxypropane, 2,2-diethoxypropane, 3,3-diemthoxypentane and 3,3-diethoxypetane.

17. The process of claim 13 wherein derivative (III) is contacted with an aqueous solution of an alkali metal hydroxide, liquid bromine is added to the resultant solution and derivative (IV) is recovered therefrom.

18. The process of claim 4 wherein derivative (III) is contacted with an aqueous solution of an alkali metal hydroxide, liquid bromine is added to the resultant solution and derivative (IV) is recovered therefrom.

19. The process of claim 11 wherein the base is selected from an alkali or alkaline earth metal hydroxide; the strong acid is selected form mineral acid or a strong organic acid; and R and R' are independently selected from hydrogen, lower alkyl, cycloalkyl, aryl or in combination represent at C$_4$-C$_6$ alkylene group.

20. The process of claim 12 wherein the base is selected from an alkali or alkaline earth metal hydroxide; the strong acid is selected from mineral acid or a strong organic acid; and R and R' are independently selected from hydrogen, lower alkyl, cycloalkyl, aryl or in combination represent a C$_4$-C$_6$ alkylene group.

* * * * *